US011276485B2

(12) United States Patent
Park et al.

(10) Patent No.: US 11,276,485 B2
(45) Date of Patent: Mar. 15, 2022

(54) MEDICATION ADHERENCE THROUGH PERSONALIZED ALERTS

(71) Applicant: International Business Machines Corporation, Armonk, NY (US)

(72) Inventors: Yoonyoung Park, Cambridge, MA (US); Hillol Sarker, Belmont, MA (US); Fang Lu, Billerica, MA (US); Uri Kartoun, Cambridge, MA (US)

(73) Assignee: International Business Machines Corporation, Armonk, NY (US)

( * ) Notice: Subject to any disclaimer, the term of this patent is extended or adjusted under 35 U.S.C. 154(b) by 448 days.

(21) Appl. No.: 16/397,575

(22) Filed: Apr. 29, 2019

(65) Prior Publication Data
US 2020/0342971 A1    Oct. 29, 2020

(51) Int. Cl.
*G16H 20/10* (2018.01)

(52) U.S. Cl.
CPC .................. *G16H 20/10* (2018.01)

(58) Field of Classification Search
CPC ......... G16H 20/10; G06F 19/30; G06F 19/32; G06F 19/34; G06F 19/3456; G06F 19/3462; G06F 19/3468; G06F 19/3475; G06F 19/3481; G06Q 50/22; G06Q 50/24
USPC ........................................................ 705/2, 3
See application file for complete search history.

(56) References Cited

U.S. PATENT DOCUMENTS

| | | | |
|---|---|---|---|
| 9,280,888 B2 | 3/2016 | Ramsdell et al. | |
| 9,858,790 B1 | 1/2018 | Goyal et al. | |
| 2013/0096953 A1 | 4/2013 | Beverly et al. | |
| 2014/0108031 A1* | 4/2014 | Ferrara | G16H 20/10 705/2 |
| 2015/0278475 A1 | 10/2015 | Shor | |
| 2017/0265819 A1 | 9/2017 | Colman et al. | |
| 2018/0046776 A1 | 2/2018 | Chalifoux | |
| 2020/0004583 A1* | 1/2020 | Kelly | G06N 20/00 |

FOREIGN PATENT DOCUMENTS

WO    WO-2020005490 A1 *    1/2020    ............. G06F 9/451

OTHER PUBLICATIONS

McCoy, Liza; "Time, self and the medication day: a closer look at the everyday work of 'adherence';" Sociology of Health & Illness vol. 31 No. 1 2009 ISSN 0141-9889, pp. 128-146 (Year: 2009).*
Kessler et al., Journal of General Internatl Medicine, vol. 33, No. 9, pp. 1536-1542, 2018.

* cited by examiner

*Primary Examiner* — Elaine Gort
*Assistant Examiner* — Christopher B Wehrly
(74) *Attorney, Agent, or Firm* — Troutman Pepper Hamilton Sanders LLP

(57) ABSTRACT

Embodiments provide a system and method for a customized alert generation for medication adherence. Medication intake instructions and user data are collected and analyzed to determine an availability model of the user to take the medication. A suggested arrangement for the user to take the medication based on the availability model is determined, and the user is alerted according to the suggested arrangement. The user provides feedback on whether the medication was taken upon receiving the alert, and the feedback trains the availability model to provide an improved suggested arrangement for taking the medication.

18 Claims, 4 Drawing Sheets

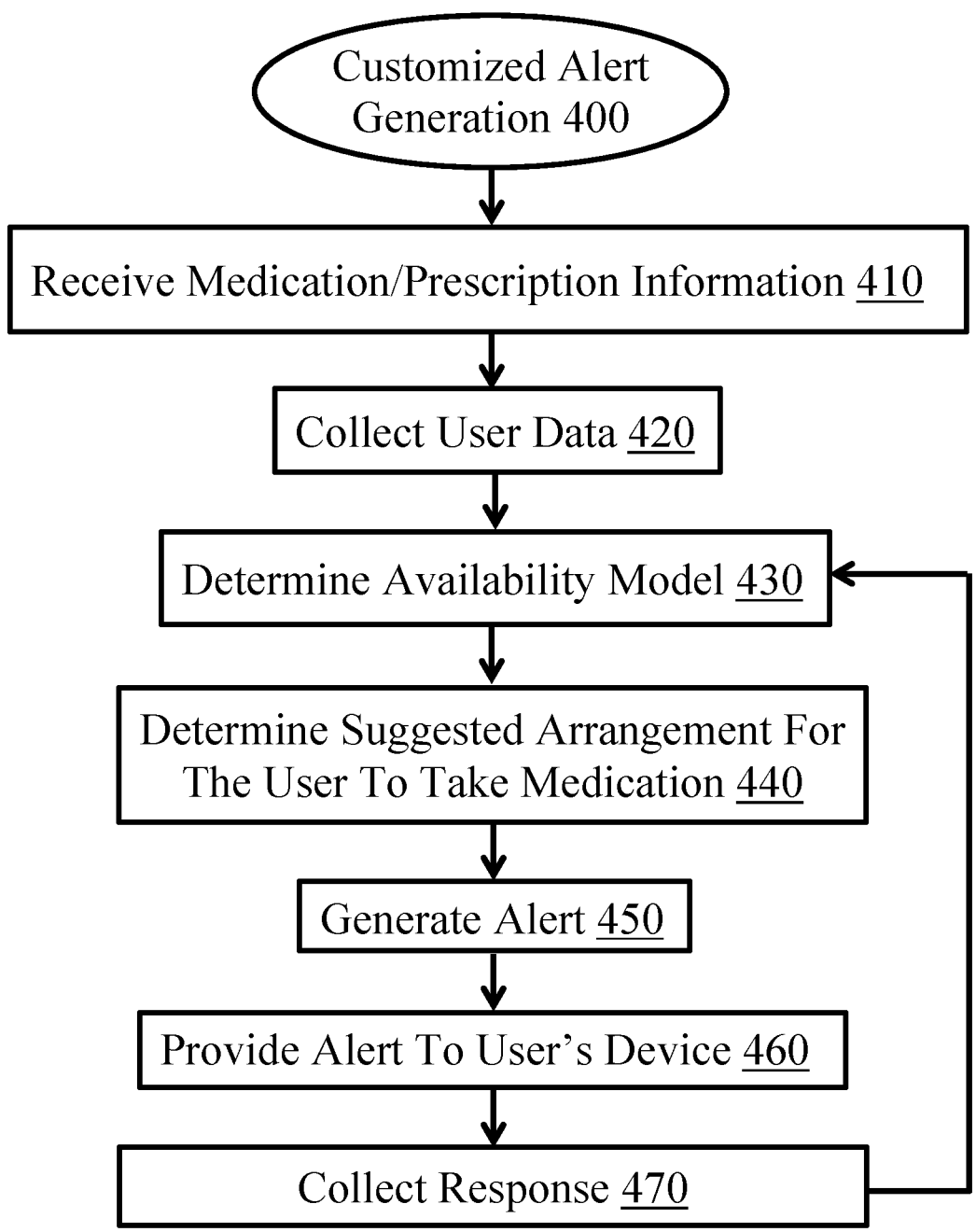

MEDICATION ADHERENCE THROUGH PERSONALIZED ALERTS

BACKGROUND

A significant problem in health care is the failure for patients to adhere to their medication instructions. For example, patients may forget to take their medication at the prescribed time, or they may take a different dose than as instructed by physicians.

The present invention generally relates to improving a patient's adherence to medication instructions. More specifically, the present invention improves a patient's medication adherence through a personalized alert corresponding to the most likely time that a patient is both physically and cognitively available to take the medication.

The efficacy of any medication is partially predicated on the patient taking the medication as prescribed. If a patient fails to take a medication on the prescribed schedule, the medication may not have the desired effect. In the case of an illness, a patient who fails to take the appropriate dose may recover more slowly or not at all. Conversely, a patient who takes a higher dose than instructed may encounter harmful side effects or even death. In the case of pain management, some medications such as opioids have a risk of addiction that comes with taking more than the prescribed dose or taking the medication more often than prescribed. For example, if a patient was prescribed a pain medication every eight hours but instead took it every four hours, then the patient may suffer an increased risk of dependency. Some medications are required to be taken before or after food or water. When those conditions are not present, the medications may not be effective, or they may cause undesirable side effects.

The issue of medication adherence is not limited to pharmacological treatments. Adherence to other forms of treatments such as medical devices or physical therapy is also a known concern. An order or recommendation for physical therapy may not be adhered to by the patient if, for instance, the patient forgets to follow-up and sufficiently accomplish the ordered therapy. For example, a patient who is advised to stretch three times a day may only remember to do so once a day or may forget altogether. Another limitation in this example is that if the stretches are to be done evenly throughout the day such as every eight hours, the patient may not do them at the appropriate intervals. One reason that a patient may not do the stretches at the appropriate intervals is that the patient may be occupied with other activities at the designated time, and it may be inconvenient or even impossible for the patient to hold off these activities and do the stretches at that time. When the patient becomes available, a common concern is that the patient forgets to accomplish the stretches. Physical therapy may also take place with a physical therapist, and patients may need to be reminded of an appointment with the physical therapist. Like pharmacological treatments, failure to adhere to physical therapy schedules may also negatively impact patient healthcare.

Failure to adhere to medical prescriptions not only has a negative impact on patient healthcare but to society as well. When patients fail to take their medications properly, they then often need additional medical care. This additional care is often costly; for example, a patient who becomes addicted to opioids may require additional treatments and resources to overcome the addiction. As another example, ensuring proper use of antibacterial medications is a critical factor in minimizing the development of antibiotic-resistant bacteria.

Conventional alerting methods are only partially effective. Such alerts are triggered at set times and/or dates without consideration of a myriad of other factors that influence whether the patient is able to take the prescribed medication, such as whether the patient is physically or cognitively available to take the medication. For example, if a patient is driving when the alert goes off, and the patient does not have the medication with him or her, then the patient cannot physically take the medication. Further, the patient may forget to take the medication when he or she is physically able to take the medication at a later time, especially if there is a long time between the time of the alert and arriving at the location of the medication. As another example, the patient may be physically able to take a particular medication, but the alert may go off while the patient is not cognitively available such as when having a conversation; when the conversation is over, the patient may forget to take the medication.

Another limitation with conventional solutions is that many medications have additional requirements in addition to dose and time for taking the medication. For instance, some medications must be taken with water and/or food. Conventional solutions do not account for these requirements.

Another limitation of conventional solutions is that they use previous events and activities to predict subsequent actions. Such solutions do not account for the patient's physical and cognitive availability to react to the alarm and actually follow the instructions for the medication.

To address the limitations specified above, one embodiment provides a medication reminder that alerts patients when they are physically and cognitively available.

SUMMARY

Embodiments of the invention provide a computer implemented method, in a data processing system comprising at least one processor and at least one memory, the at least one memory comprising instructions which are executed by the at least one processor to cause the at least one processor to be specifically configured to execute the operations of the method for an intelligent medication reminder, the method receiving a medication intake instruction for a patient; collecting patient data comprising one or more of a location, activity, or engagement of a patient; generating an availability model based on the patient data and the medication intake instruction; determining a suggested arrangement for the patient to take the medication based on the availability model; generating an alert corresponding to the suggested arrangement for the patient to take the medication; and providing the alert to a user device associated with the patient.

Embodiments can further provide a method comprising collecting a response to the alert; and using the response to train the availability model.

Embodiments can further provide a method wherein the patient data comprises a health condition of the patient.

Embodiments can further provide a method comprising wherein the availability model comprises: a physical availability for the patient to take the medication; and a cognitive availability for the patient to take the medication.

Embodiments can further provide a method comprising wherein the availability model identifies a plurality of opportunities for the patient to take the medication, wherein each opportunity is weighted based on a likelihood that the patient is available to take the medication.

Embodiments can further provide a method wherein each opportunity is further weighted based on feedback from the patient, wherein the feedback includes whether the medication was taken.

Embodiments can further provide a method wherein the suggested arrangement for the patient to take the medication comprises the opportunity with the highest likelihood that the patient is available to take the medication and will react to take the medication.

Embodiments can further provide a method comprising wherein the alert generates at least one of a sound, vibration, or text prompt to take the medication.

Embodiments can further provide a method comprising wherein the response comprises an indication that the patient is unavailable using a snooze button, a hand gesture, or a speech-based command.

Embodiments can further provide a method comprising wherein the response is shared with a third party.

In another illustrative embodiment, a computer program product comprising a computer usable or readable medium having a computer readable program is provided. The computer readable program, when executed on a processor, causes the processor to perform various ones of, and combinations of, the operations outlined above with regard to the method illustrative embodiment.

In yet another illustrative embodiment, a system is provided configured to perform various ones of, and combinations of, the operations outlined above with regard to the method illustrative embodiment.

Additional features and advantages of this disclosure will be made apparent from the following detailed description of illustrative embodiments that proceeds with reference to the accompanying drawings.

BRIEF DESCRIPTION OF THE DRAWINGS

The foregoing and other aspects of embodiments of the present invention are best understood from the following detailed description when read in connection with the accompanying drawings. For the purpose of illustrating the invention, there is shown in the drawings embodiments that are presently preferred, it being understood, however, that embodiments of the invention are not limited to the specific instrumentalities disclosed. Included in the drawings are the following Figures:

FIG. 4 depicts a flow chart for a medication adherence system according to embodiments described herein.

DETAILED DESCRIPTION

Figure 1:
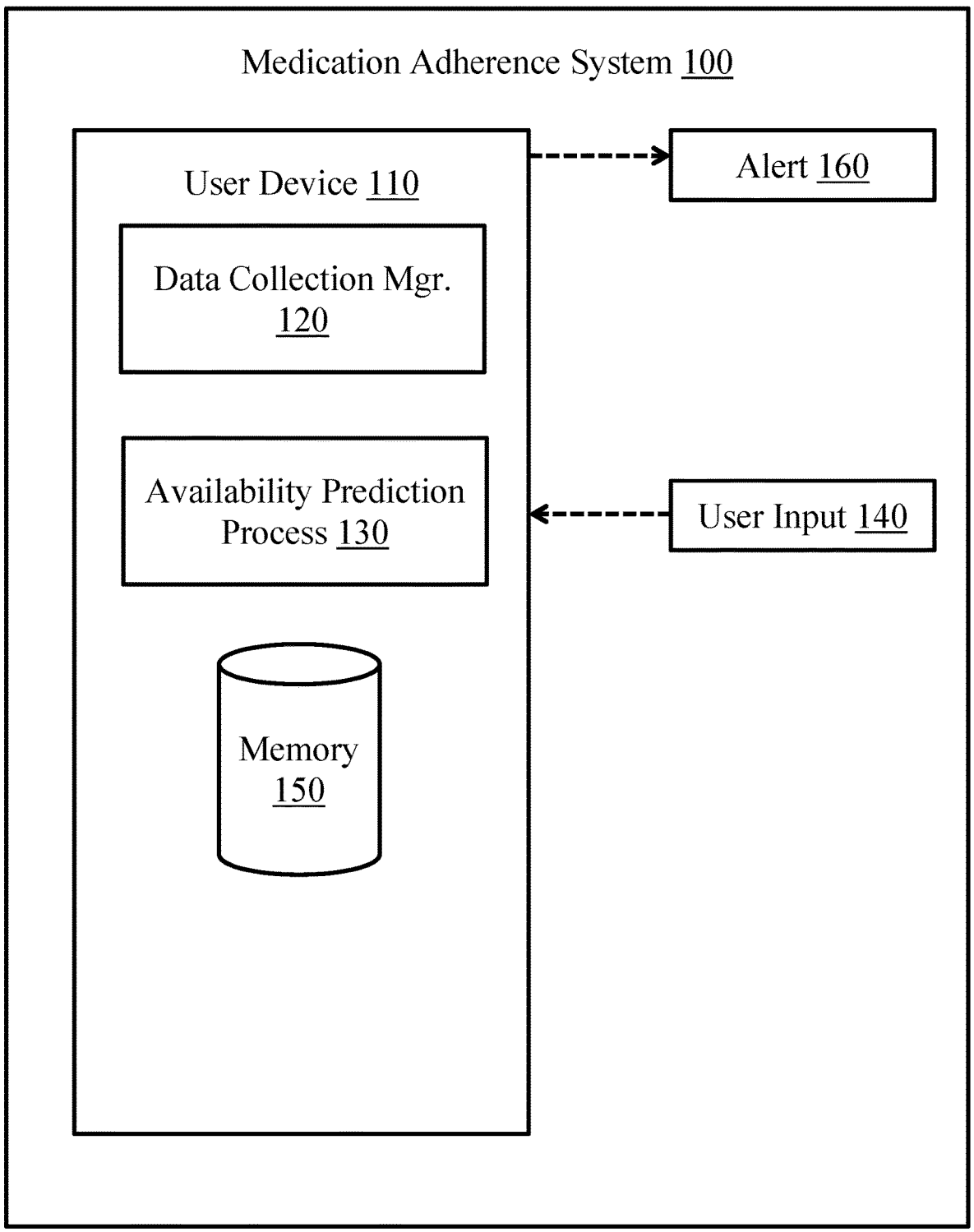
FIG. 1 depicts an embodiment of a medication adherence system according to embodiments described herein.

The present description and claims may make use of the terms "a," "at least one of," and "one or more of," with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the example provided herein without departing from the spirit and scope of the present invention.

Embodiments of the present invention may be a system, a method, and/or a computer program product. The computer program product may include a computer-readable storage medium (or media) having the computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a head disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network (LAN), a wide area network (WAN) and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including LAN or WAN, or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer-readable program instructions may also be loaded onto a computer, other programmable data processing apparatus, or other device to cause a series of operations steps to be performed on the computer, other programmable apparatus, or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical functions. In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Aspects of the present invention may be implemented on a cognitive system. As an overview, a cognitive system is a specialized computer system, or set of computer systems, configured with hardware and/or software logic (in combination with hardware logic upon which the software executes) to emulate human cognitive functions. These cognitive systems apply human-like characteristics to convey and manipulate ideas which, when combined with the inherent strengths of digital computing, can solve problems with high accuracy and resilience on a large scale. IBM Watson™ is an example of one such cognitive system which can analyze the context of speech and filter objectionable portions with human-like accuracy at speeds far faster than human beings and on a much larger scale. In general, such cognitive systems are able to perform the following functions:

1. Ingest and process vast amounts of structured and unstructured data;
2. Generate and evaluate hypotheses;
3. Weigh and evaluate responses that are based only on relevant evidence;
4. Provide situation-specific advice, insights, and guidance;
5. Improve knowledge and learn with each iteration and interaction through machine learning processes;
6. Enable decision making at the point of impact (e.g., when to send an alert);
7. Scale in proportion to the task;
8. Deduce physical availability from patient data (e.g., location, medical condition);
9. Deduce cognitive availability from patient data (e.g., social engagement, activity);
10. High degree of relevant recollection based on relevant data points (e.g., physical and cognitive activity); and
11. Predict and sense with situational awareness that mimics human cognition based on experiences.

FIG. 1 illustrates an exemplary diagram of one illustrative embodiment of a medication adherence system 100. In an embodiment, the medication adherence system 100 comprises a user device 110 that is carried or worn by the patient. The user device 110 may comprise any type of mobile or wearable computer with various sensors. Examples of such user devices 110 include a smartphone and a smartwatch. Other patient user devices 110 with sensors could also be used such as laptop computers, notebook computers, or other such devices with internal or external sensors such as those contained in smartphones and smartwatches. These sensors typically include one or more of the following: camera, microphone, global positioning system (GPS), accelerometer, gyroscope, magnetometer, proximity sensor, ambient light sensor, touchscreen sensors, fingerprint sensor, pedometer, barcode/QR code sensors, barometer, heart rate sensor, thermometer, air humidity sensor, and the like. This invention contemplates the use of any other sensors that can be incorporated into or connected to the user device 110 to provide information related to the user and the user's environment.

The user device 110 in an embodiment includes a data collection manager 120 that can access the data collected by the sensors on the user device 110. The data collection manager 120 may comprise software that operates in a computing environment on the user device 110, or in another embodiment, it may be installed in a remote computing environment. In an embodiment, the data collection manager 120 is installed in a network computing environment and interfaces with the sensor data on the user device 110 via a remote connection. A remote connection may comprise a wired or wireless internet connection between the remote computing environment and the user device 110. In addition to internet connections, other remote connections may include BlueTooth, WiFi, or other wired or wireless communication modalities.

The data gathered from the sensors on the user device 110 by the data collection manager 120 provides information about the user and the user's environment. For example, GPS provides information on the location of the user device 110, and if that device is worn by the user or otherwise physically present with the user, then the location of the user is also known. Location can also be determined by mobile devices using a variety of other technologies in addition to or instead of GPS. For example, some mobile devices are able to determine location through triangulation based on cell tower location. Other location methods used by mobile devices may include determining the location of the user device 110 based on the known location of WiFi routers that the user device 110 is connected with.

GPS can also indicate whether the user device 110 is moving, and by association, whether the user who is wearing or physically possessing the user device 110 is also moving. Other sensors such as the accelerometer, gyroscope, and the magnetometer (compass) provide additional information regarding the movement, and this information can be used alone or in combination with GPS. The magnetometer provides the direction of the movement. The accelerometer, pedometer, and gyroscope provide additional information on the movement, such as whether the user is running, walking, or performing some other exercise. Wearable devices such as smartwatches that are worn on the user's wrist can determine if the user's arm is moving up or down with accelerometer and gyroscope sensors.

Other sensors provide additional information about the user and the user's surroundings. The ambient light sensor can detect whether it is daylight or night. The thermometer determines the temperature. A heart rate sensor can determine whether the user is exercising or resting.

The microphone in a user device 110 can indicate if the user is in a conversation if it is detecting speech. The microphone can detect speech, whether from the user or from another person. In some embodiments, the detected speech can be processed to determine the type of speech, such as speech from a person standing near the user or speech from the user. For example, if speech is detected alternatively from the user and another person, it can be inferred that a conversation is taking place. To determine if speech is from the user in an embodiment, a speech analysis is performed to match the detected speech with a predetermined speech pattern associated with the user.

Instead of detecting conversation, the input from the microphone can be also used to determine if the user is watching a television program or a movie. For example, if speech is being detected from a television show, advertisements that are played periodically can be detected to indicate that the user is watching television. To detect advertisements, speech recognition software is used to identify common characteristics of advertisements on television. For example, the volume of commercials is typically louder than the volume of the television program. Other means for detecting commercials is based on the words used typically in advertisements such as common product and trade names, references to pricing, sales, etc. Movies that are being played on television can also be detected using a similar speech analysis that detects common characteristics such as continual dialog, music, and sound effects.

In an embodiment, speech recognition software can also be used to determine the context of the recorded speech. For example, speech can be analyzed to determine if the conversation is part of a business meeting in a conference room, conversation at a party, conversation at a doctor's office, or conversation in other situations. Speech recognition software determines the context from the words spoken, how they were spoken (e.g., loud, quickly, hushed, etc.), and the ambient noise (e.g., music, wind, cars, etc.) around the speech. Numerous other factors can also be used to determine the context of the speech.

The data collection manager 120 also obtains information in addition to information from sensors. In an embodiment, the data collection manager 120 identifies the use of the user device 110. For example, the data collection manager 120 can determine if the user device 110 is currently being used and how it is being used by determining if an application (or "app") on the user device 110 is being used. Further information can be obtained, for example, such as which app is being used. If the user is using an email app, then it can be inferred that the user is checking email. As another example, if a game is being used, then it can be inferred that the user is playing a game. Further data can be collected on how the computer applications are being used such as in the case of a video game, what game is being played.

Other information collected by the data collection manager 120 may include data describing the user's activities and appointments. For example, the data collection manager 120 can collect information from the user's calendar application on the user device 110 as well as the current date and time. In an embodiment, data from the calendar application on the user device 110 may include appointments, the location of those appointments, and the time of the appointments. Other similar information is also contemplated.

Due to the extent of information collected by the data collection manager 120, privacy settings can optionally be managed by the user. In an embodiment, the user can select the amount of information collected. For example, the user can disable the speech recognition function to preclude "eavesdropping" of speech detected on the microphone. In an embodiment, location information can be disabled. Other information can be disabled or enabled from the collection by the data collection manager 120. In an embodiment, the level of detail of information collected can optionally be varied by the user. For example, a user's location may be determined only in a general vicinity such as within a five-mile radius of the actual location. Other user data can also be limited in a similar fashion.

The user device 110 comprises an availability prediction process 130. The availability prediction process 130 may comprise software that operates in a computing environment on the user device 110, or in another embodiment, it may be installed in a remote computing environment. In an embodiment, the availability prediction process 130 is installed in a network computing environment. The availability prediction process 130 generates an availability model for the user (i.e., patient) to identify probabilities that a user is ready and able to respond to an alert such as by taking medication or performing an activity such as a physical therapy exercise. References to taking medication, unless otherwise specified, should be understood to also include doing any ordered, recommended, or scheduled activity.

The availability prediction process 130 uses one or more of the data collected by the data collection manager 120 in the determination of the probability that the user is available to take medication. If the user is engaged in an activity, then the user will not likely be cognitively able to take the medication. If the user is not physically near the medication, the user will not be physically able to take the medication. For example, if the user is going for a run, the user is engaged in exercise away from home, and not as likely to be available to take the medication because the user is not physically available to access the medication and not cognitively available because the user is occupied with jogging. It can be determined if the user is going for a run by the GPS location, speed, and direction of the user, as well as by using data from other sensors such as one or more of the accelerometer, pedometer, and gyroscope sensors. Other sensors and combinations of sensors can also be used to determine if the user is jogging. For example, the user's calendar application might indicate "exercise" at the specific time and date that other GPS, accelerometer, pedometer, and/or gyroscope data indicates the user is jogging and not available to take the medication.

Other user activity that would indicate that a user is not cognitively available to take medication may include being engaged in a conversation with someone either in person, over the phone, or via text message. The data collection manager 120 determines if the user is engaged in a conversation if the microphone on the user device 110 is being used. In the case of a text message conversation, the data collection manager 120 determines if a text message application is being used by the user. If the user is engaged in a conversation, then the user is not cognitively available, and the probability that the user will take the medication is low.

The invention contemplates detecting other types of user engagement through the combination of one or more data collected by the data collection manager 120. In an embodiment, if it is detected that user device 110 is being used then it can be inferred that the user is less likely to be cognitively available to take the medication. For example, if the email application on the user device 110 is being used, then it can be inferred that the user is busy with email. If a game is open on the user device 110, then it can be inferred that the user is busy with the game. Similarly, other applications may also indicate that the user is unavailable. However, some applications may not necessarily indicate that the user is busy. In the instance in which the user uses a weather application, it may be inferred that the user is only going to be quickly checking the weather and then be cognitively available to take medication shortly after the weather app is opened. Thus, the type of application that is open and being used on the user device 110 is relevant to the weighting of the probability that the user will be cognitively available by the availability prediction process 130.

In an embodiment, the user can provide user input 140 that is considered by the availability prediction process 130. For example, the user can input the times that the user would like to take the medication. The user can input the times that the user is unavailable to take the medication such as when working, picking up children, or other times that may not be entered in a personal calendar on the user device 110. These user inputs are considered by the availability prediction process 130 alone or in combination with one or more of the other data discussed to weight the probability that the user is cognitively available to take the medication.

Other user input 140 to the user device 110 can also be provided to the availability prediction process 130 such as any data relevant to the medication intake and adherence. For example, any comorbidities, allergies, or disabilities can be an input. The user, the user's doctor, a relative, or other caregivers can provide such input. In an embodiment, the medication intake instructions are also used by the availability prediction process 130 to generate the availability model.

The availability prediction process 130 receives the above-mentioned data and generates an availability model. The availability model determines the probabilities that the user will be available to take the medication. In other words, the availability model comprises the times in which the user is most likely to respond to an alert and actually take the medication.

In addition to cognitive availability, physical availability to take the medication is also determined by the availability prediction process 130. A user must not only respond to an alert to take the medication, but to take the medication, the user must be physically able to take the medication. For example, if the medication is routinely kept at the user's home, and the user is not at home, then the probability of taking the medication is low. On the other hand, if the medication is typically carried on the user's person, then the fact that the user is not home would not necessarily negatively affect the probability of taking the medication.

The availability prediction process 130 generates an availability model of the likelihood that the user is physically able to take the medication. Data considered by the availability prediction process 130 comprises one or more of the user's location, the medication intake instructions, and any physical restrictions of the user. The location of the user can be determined, for example, by locations sensors in the user device 110 such as the GPS sensors.

Medication intake instructions dictate how and when the medication is to be taken, which affects the user's physical availability to take the medication. For example, medication that is to be taken with water requires that the user have water to physically be able to take the medication. Medication intake instructions can be input by the user, medical provider (doctor, physical therapist, nurse, etc.), pharmacist, family members, caregiver, or other parties. User input 140 comprising medication intake instructions can be input directly into the user device 110. Medication intake instructions can also be input indirectly. In an embodiment, user input 140 comprises the medication, and associated intake instructions are retrieved from memory 150. Thus, when the medication is specified in the medication adherence system 100, associated instructions for taking that medication are retrieved from a memory 150 and input to the availability prediction process 130 for use in the availability model.

In an embodiment, the physical availability of a user to take medication can be determined using data (in addition to the data previously discussed) from sensors on wearable user devices 110 that indicate hand and arm movement in a pattern that indicates the user is eating. If the movement of the user's arm on which the wearable user device 110 resides causes the various accelerometer, gyroscope, and other sensors on the user device 110 to indicate a user is bringing food and/or water to the user's mouth, then the availability prediction process 130 will determine that the user is physically available to take medication that requires food and/or water.

In an embodiment, a "just-in-time" alert 160 using one or more of a sound, vibration, visual, or text prompt can be issued when it is determined that the user is about to eat and/or drink, if the medication is to be taken prior to food and/or water intake. Similarly, such an alert 160 can be generated in other situations such as in the instance in which medication is to be taken with or immediately after eating or drinking.

Physical restrictions of the user are also considered in the availability prediction process 130. For example, if a user is required to do physical therapy that requires exercise in a pool, then the user would not be physically able to do the therapy unless physically located at a pool. Known locations of pools where the user has done the physical therapy are stored in memory 150. When the availability prediction process 130 determines the user is at or approaching a pool based on GPS alone or in combination with other data (e.g., calendar data indicating a pool session), then the user is physically able to do therapy.

In an embodiment, the physical and cognitive availability can be determined as separate models and combined into a total availability model. In an embodiment, the availability model can be determined by cognitive systems that use artificial intelligence and/or machine learning to output the weighted availabilities for the user to be physically able to take the medication and cognitively available to actually respond to an alert to do so.

Based on the most likely determined availability, the medication adherence system produces an alert 160 on the user device 110 to the user. The alert 160 may comprise an audible alarms, visual cues, vibrations, text alerts, emails, or other alerts. The alert 160 comprises a suggested arrangement for the user to take the medication based on the determined most likely availability of the user. For example, if the medication is required to be taken with food, then the alert 160 may provide a suggested arrangement comprising a text message that is sent during dinner time while the user is at home that tells the user what medication to take and how much.

In an embodiment, the alert 160 is also sent in addition and/or alternatively to one or more other parties including a medical professional, friend, caregiver, family member, or other parties who is authorized to receive the alert 160.

In an embodiment, separate alerts 160 can be generated for different medications. For example, a user who needs to take multiple medications with different intake requirements can have a separate alert 160 for each medication. For instance, the alerts 160 can have different sounds.

When the user receives the alert 160, in an embodiment, the user has the option of indicating whether the user will take the medication. Such an indication can optionally silence the alert. In an embodiment, if the user ignores the alert for a period of time, the patient medication adherence system 100 will conclude that the user is not going to take the medication. In an embodiment, the user can "snooze" the alarm for a set period of time or indicate a preferred time for the alarm to go off again. In an embodiment, a snooze button indicates that the user is unavailable to take the medication. Other means of receiving a response from the user include, but are not limited to, a hand gesture or a speech-based command. A hand gesture enables a user to easily silence ("snooze") the alarm without the need to press a button. The hand gesture can be optically detected by a camera that can detect motion. The camera can optionally detect light in a wide variety of the optical spectrum including visible and infrared spectrums. A speech-based command enables a user to silence ("snooze") the alarm without making any physical movements, which is advantageous for physically disabled users. In an embodiment, the user can change the word(s) that enable the snooze function. In an embodiment, the word(s) used chosen by the user for the snooze function can be chosen on a language independent basis.

The user's response to the alarm 160 is provided back to the availability prediction process 130 to train the availability model. The availability prediction process 130 uses this feedback to improve the suggested arrangement for the user to take the medication. For example, if the user routinely snoozes the alarm at a particular time and then indicates that the medication is taken 30 minutes later, then the availability model may choose a time 30 minutes later to better reflect when the user is actually going to take the medication. The availability models, user responses, and other data are stored in memory 150.

Figure 2:
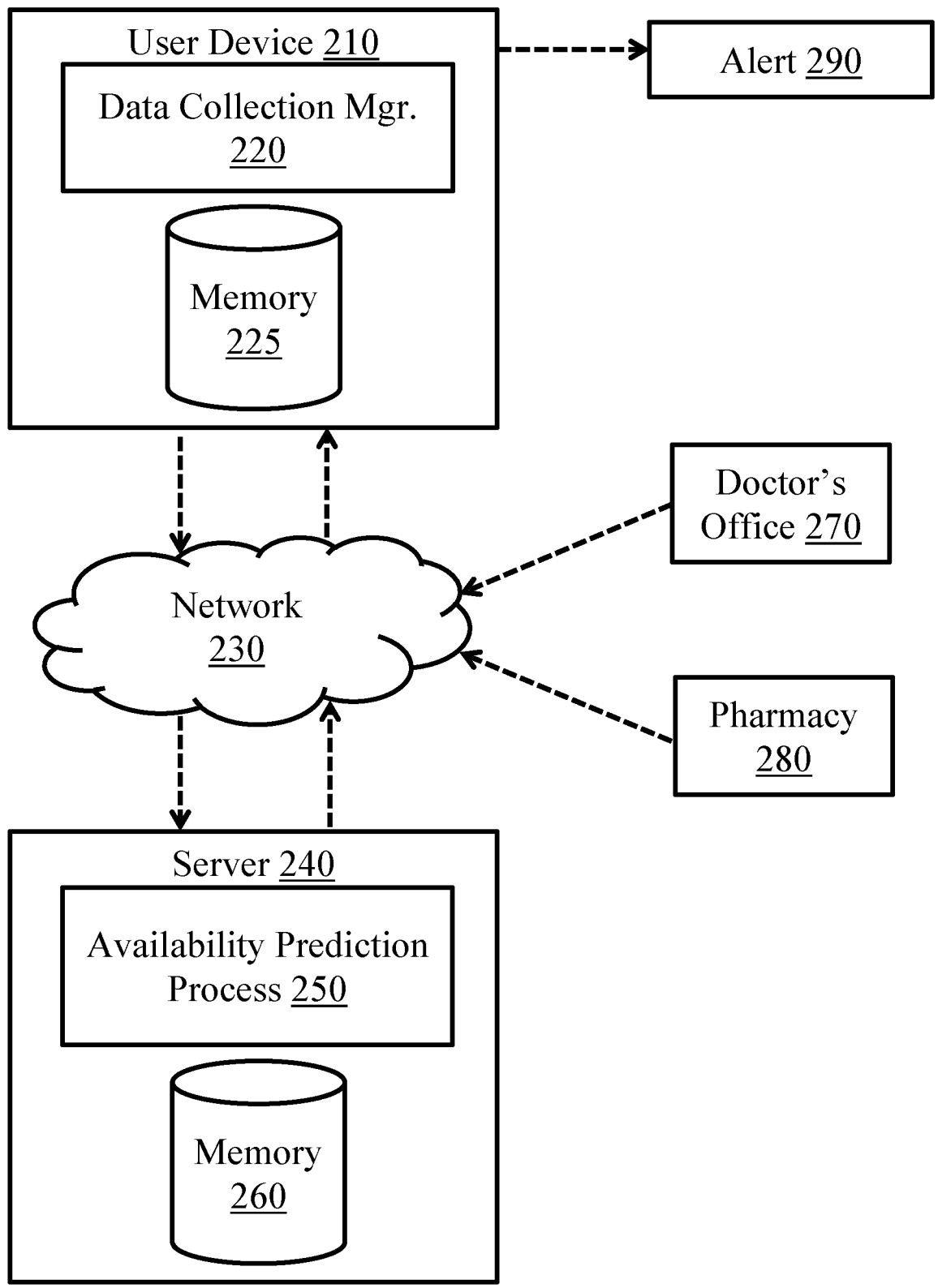
FIG. 2 depicts a cloud-based medication adherence system according to embodiments described herein.

FIG. 2 depicts a cloud-based medication adherence system 200. In an embodiment, a mobile user device 210 may be connected to a network 230 comprising the internet, WiFi network, BlueTooth, or other networks in which data can be communicated. The data collection manager 220 collects the sensor data as described above with respect to FIG. 1. This data may be stored in memory 225. In an embodiment, this data is transmitted over network 230 to server 240.

In an embodiment, server 240 comprises the availability prediction process 250. Server 240 is located remotely from user device 210. The availability prediction process 250 functions as described above with respect to FIG. 1. Server 240 is connected to the user device 210 via network 230. In this arrangement, server 240 determines the suggested arrangement for the user to take the medication and determines when and how the alert 290 should be sent. After the user device 210 receives the instructions from server 240 to send the alert 290, user device 210 sends alert 290. The alert 290 may comprise any one or more of an audible alarm, visual cues, vibration, text alert, email, or other alerts. In an embodiment, the alert 290 can also be sent by server 240 over network 230 to other people including medical professionals, family members, caregivers, friends, or others. Server 240 comprises memory 260, which stores the determined availability information.

In an embodiment, medication instructions can be provided remotely by a medical professional at the doctor's office 270 or from a pharmacy 280. For example, a doctor who prescribes a medication with a specified dosage can transmit that prescription electronically to the pharmacy (not shown), and the intake instructions can also be transmitted through network 230 to the availability prediction process 250 on server 240. This enables the user to receive medication alerts without the user needing to input medication instructions. Likewise, the pharmacy 280 can also provide medication intake instructions over network 230 to the availability prediction process 250. Another benefit to remote access by medical and pharmacology professionals is that medication intake instructions can be easily modified without user involvement.

In an embodiment, feedback from the user regarding whether or not the medication was taken can be provided to the availability prediction process 250 via network 230. In an embodiment, feedback can be provided to the user device 210, and the user device 210 can then transmit the feedback to the availability prediction process 250 via network 230.

Figure 3:
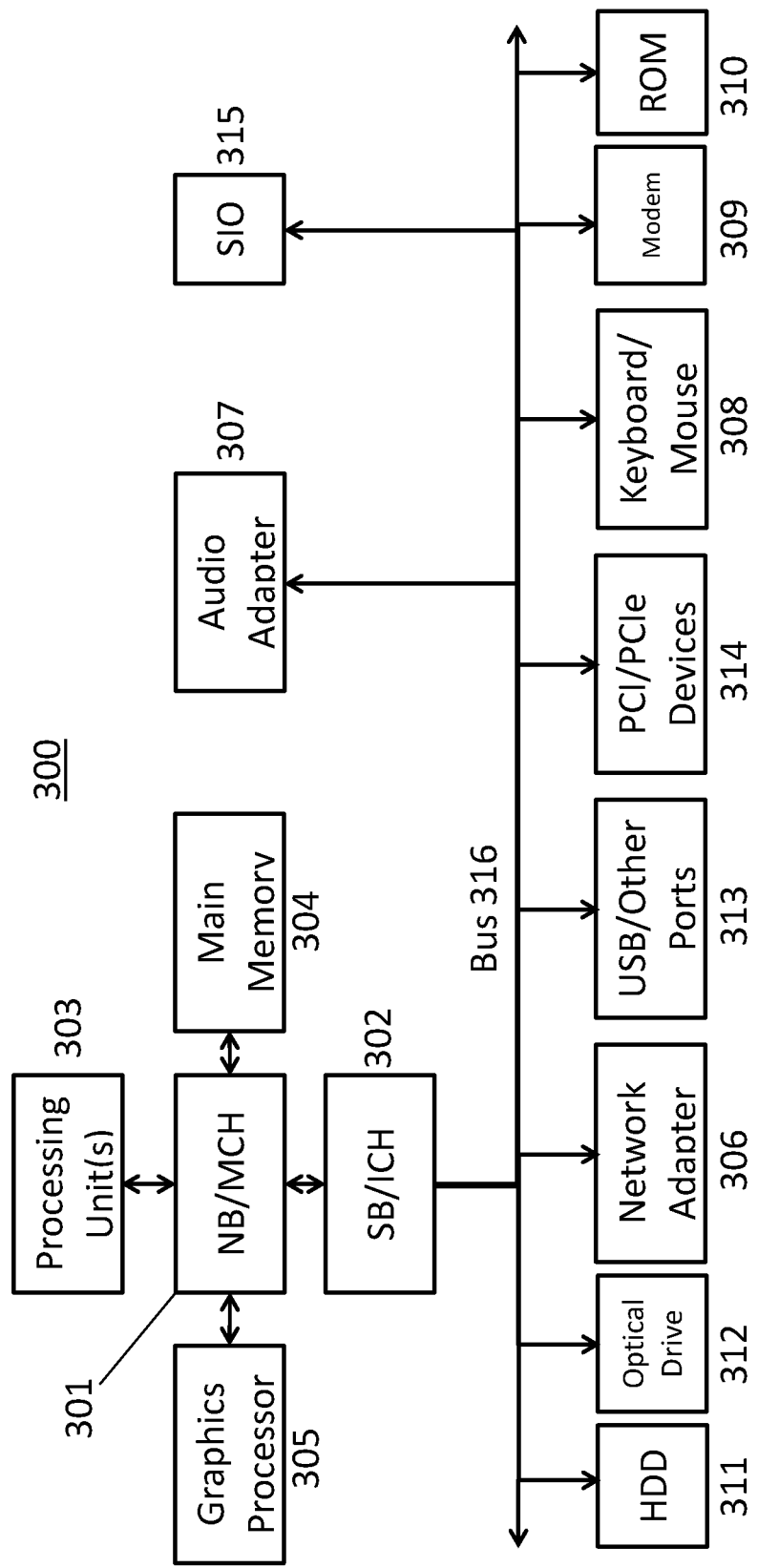
FIG. 3 is a block diagram of an example system in which aspects of the illustrative embodiments may be implemented.

FIG. 3 is a block diagram of an example data processing system 300 in which aspects of the illustrative embodiments, such as the inspectors, can be implemented. Data processing system 300 is an example of a computer, such as a server or a client, in which computer usable code or instructions implementing the process for illustrative embodiments of the present invention are located. In one embodiment, FIG. 3 represents a server computing device, such as a server, which implements the network tracking system described herein.

In the depicted example, data processing system 300 can employ a hub architecture including a north bridge and memory controller hub (NB/MCH) 301 and south bridge and input/output (I/O) controller hub (SB/ICH) 302. Processing unit 303, main memory 304, and graphics processor 305 can be connected to the NB/MCH 301. Graphics processor 305 can be connected to the NB/MCH 301 through an accelerated graphics port (AGP).

In the depicted example, the network adapter 306 connects to the SB/ICH 302. The audio adapter 307, keyboard and mouse adapter 308, modem 309, read-only memory (ROM) 310, hard disk drive (HDD) 311, optical drive (CD or DVD) 312, universal serial bus (USB) ports and other communication ports 313, and the PCI/PCIe devices 314 can connect to the SB/ICH 302 through bus system 316. PCI/PCIe devices 314 may include Ethernet adapters, add-in cards, and PC cards for notebook computers. ROM 310 may be, for example, a flash basic input/output system (BIOS). The HDD 311 and optical drive 312 can use an integrated drive electronics (IDE) or serial advanced technology attachment (SATA) interface. The super I/O (SIO) device 315 can be connected to the SB/ICH 302.

An operating system can run on processing unit 303. The operating system can coordinate and provide control of various components within the data processing system 300. As a client, the operating system can be a commercially available operating system. An object-oriented programming system, such as the Java™ programming system, may run in conjunction with the operating system and provide calls to the operating system from the object-oriented programs or applications executing on the data processing system 300. As a server, the data processing system 300 can be an IBM® eServer™ System p® running the Advanced Interactive Executive operating system or the Linux operating system. The data processing system 300 can be a symmetric multiprocessor (SMP) system that can include a plurality of processors in the processing unit 303. Alternatively, a single processor system may be employed.

Instructions for the operating system, the object-oriented programming system, and applications or programs are located on storage devices, such as the HDD 311, and are loaded into the main memory 304 for execution by the processing unit 303. The processes for embodiments of the medication adherence system 100 can be performed by the processing unit 303 using computer usable program code, which can be located in a memory such as, for example, main memory 304, ROM 310, or in one or more peripheral devices.

A bus system 316 can be comprised of one or more busses. The bus system 316 can be implemented using any type of communication fabric or architecture that can provide for a transfer of data between different components or devices attached to the fabric or architecture. A communication unit such as the modem 309 or network adapter 306 can include one or more devices that can be used to transmit and receive data.

Those of ordinary skill in the art will appreciate that the hardware depicted in FIG. 3 may vary depending on the implementation. Other internal hardware or peripheral devices, such as flash memory, equivalent non-volatile memory, or optical disk drives may be used in addition to or in place of the hardware depicted. Moreover, the data processing system 300 can take the form of any of a number of different data processing systems, including but not limited to, client computing devices, server computing devices, tablet computers, laptop computers, telephone or other communication devices, personal digital assistants, and the like. Essentially, data processing system 300 can be any known or later developed data processing system without architectural limitation.

FIG. 4 depicts a flow chart for a customized alert generation 400. At step 410, the medication, prescription, or other instructions is received. As previously discussed, this information can comprise medication intake instructions, physical therapy instructions, reminders, or other types of prompts to the user.

At step 420, the user data is collected. User data comprises data associated with the user that can be used by the availability model. As previously discussed, user data may comprise the location, activity, and engagement of the user as determined by sensors and data from the user's device. Other user data may comprise user-specific information such as the time that the user would like to take the medication, any user-specific needs such as those associated with a disability, allergy, or other health condition. User data may also comprise information related to the user's health conditions, such as those detected by a heart rate monitor, glucose monitor, or other such health monitors.

At step 430, an availability model is generated. The availability model is generated based on the user data collected at step 420 and the medication intake information collected at step 410. Step 430 results in a model of the availability of the user to be physically able to take the medication and actually respond to the alert to take the medication.

At step 440, a suggested arrangement for the user to take the medication is determined from the generated model. The suggested arrangement comprises the most likely arrangement for the user to take the medication. For example, the suggested arrangement for medication that must be taken before eating might be an alert 15 minutes before a scheduled lunch appointment at a restaurant 10 minutes from the user's current location.

At step 450, an alert is generated based on the suggested arrangement.

At step 460, the alert is provided to the user's device. In an embodiment, the alarm can also be provided to another's device.

At step 470, a response is collected from the user. As previously discussed, the response can be collected by the user's device and communicated to the availability model to improve the determination of the availability model 430. In an embodiment, the response can be collected in other devices and communicated via the internet to the availability model. The availability model learns from the feedback using artificial intelligence and machine learning. As a result, the determined suggested arrangement for the user to take the medication 440 is improved.

The system and processes of the figures are not exclusive. Other systems, processes, and menus may be derived in accordance with the principles of embodiments described herein to accomplish the same objectives. It is to be understood that the embodiments and variations shown and described herein are for illustration purposes only. Modifications to the current design may be implemented by those skilled in the art, without departing from the scope of the embodiments. As described herein, the various systems, subsystems, agents, managers, and processes can be implemented using hardware components, software components, and/or combinations thereof. No claim element herein is to be construed under the provisions of 35 U.S.C. 112, sixth paragraph, unless the element is expressly recited using the phrase "means for."

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. A computer implemented method, in a data processing system comprising at least one processor and at least one memory, the at least one memory comprising instructions which are executed by the at least one processor to cause the at least one processor to be specifically configured to execute the operations of the method for an intelligent medication reminder, comprising:
    receiving a medication intake instruction for a patient and a medication;
    collecting patient data by a user device associated with the patient, wherein the patient data comprises one or more of a location, activity, or engagement of a patient;
    generating, by a cognitive system using machine learning, a total availability model based on the patient data and the medication intake instruction by:
        identifying a plurality of opportunities for the patient to take the medication,
        weighting each of the plurality of opportunities based on a likelihood that the patient is cognitively available to take the medication, wherein the likelihood that the patient is cognitively available is based the patient's engagement in an activity,
        generating a cognitive availability model based on the plurality of opportunities weighted based on the likelihood that the patient is cognitively available to take the medication,
        weighting each of the plurality of opportunities based on a likelihood that the patient is physically available to take the medication, wherein the likelihood that the patient is physically available is based on the patient's physical ability to take the medication, wherein the likelihood that the patient's physical ability to take the medication is based on a physical restriction, wherein the physical restriction comprises a physical requirement to take the medication,
        generating a physical availability model based on the plurality of opportunities weighted based on the likelihood that the patient is physically available to take the medication, and
        combining the cognitive availability model and the physical availability model to generate the total availability model;
    determining a suggested arrangement for the patient to take the medication based on the total availability model, wherein the suggested arrangement for the patient to take the medication comprises the opportunity with the highest likelihood that the patient is available to take the medication and will react to take the medication;
    generating an alert corresponding to the suggested arrangement for the patient to take the medication;
    providing the alert to a user device associated with the patient;
    receiving a response from the user device, wherein the response indicates whether or not the patient will take the medication; and
    training the total availability model based on the response and the time the response was provided to the user device.

2. The computer implemented method of claim 1, wherein the patient data comprises a health condition of the patient.

3. The computer implemented method of claim 1, wherein each opportunity is further weighted based on feedback from the patient, wherein the feedback includes whether or not the medication was taken.

4. The computer implemented method of claim 1, wherein the alert generates at least one of a sound, vibration, or text prompt to take the medication.

5. The computer implemented method of claim 1, wherein the response comprises an indication that the patient is unavailable through use of a snooze button.

6. The computer implemented method of claim 1, wherein the response is shared with a third party.

7. A computer program product for an intelligent medication reminder, the computer program product comprising a computer readable storage medium having program instructions embodied therewith, the program instructions executable by a processor to cause the processor to:
    receive a medication intake instruction for a patient and a medication;
    collect patient data by a user device associated with the patient, wherein the patient data comprises one or more of a location, activity, or engagement of a patient;
    generate, by a cognitive system using machine learning, a total availability model based on the patient data and the medication intake instruction by:
        identifying a plurality of opportunities for the patient to take the medication,
        weighting each of the plurality of opportunities based on a likelihood that the patient is cognitively available to take the medication, wherein the likelihood that the patient is cognitively available is based the patient's engagement in an activity,
        generating a cognitive availability model based on the plurality of opportunities weighted based on the likelihood that the patient is cognitively available to take the medication,
        weighting each of the plurality of opportunities based on a likelihood that the patient is physically available to take the medication, wherein the likelihood that the patient is physically available is based on the patient's physical ability to take the medication, wherein the likelihood that the patient's physical ability to take the medication is based on a physical restriction, wherein the physical restriction comprises a physical requirement to take the medication,
        generating a physical availability model based on the plurality of opportunities weighted based on the likelihood that the patient is physically available to take the medication, and
        combining the cognitive availability model and the physical availability model to generate the total availability model;
    determine a suggested arrangement for the patient to take the medication based on the total availability model, wherein the suggested arrangement for the patient to take the medication comprises the opportunity with the highest likelihood that the patient is available to take the medication and will react to take the medication;

generate an alert corresponding to the suggested arrangement for the patient to take the medication;

provide the alert to a user device associated with the patient;

receive a response from the user device, wherein the response indicates whether or not the patient will take the medication; and train the total availability model based on the response and the time the response was provided to the user device.

8. The computer program product of claim 7, wherein the patient data comprises a health condition of the patient.

9. The computer program product of claim 7, wherein each opportunity is further weighted based on feedback from the patient, wherein the feedback includes whether or not the medication was taken.

10. The computer program product of claim 7, wherein the response comprises an indication that the patient is unavailable through use of a snooze button.

11. The computer program product of claim 7, wherein the response is shared with a third party.

12. A system comprising:
a memory;
a processor in communication with the memory; and
program instructions executable by the processor via the memory to cause the processor to:
  receive a medication intake instruction for a patient and a medication;
  collect patient data by a user device associated with the patient, wherein the patient data comprises one or more of a location, activity, or engagement of a patient;
  generate, by a cognitive system using machine learning, a total availability model based on the patient data and the medication intake instruction by:
    identifying a plurality of opportunities for the patient to take the medication,
    weighting each of the plurality of opportunities based on a likelihood that the patient is cognitively available to take the medication, wherein the likelihood that the patient is cognitively available is based the patient's engagement in an activity,
    generating a cognitive availability model based on the plurality of opportunities weighted based on the likelihood that the patient is cognitively available to take the medication,
    weighting each of the plurality of opportunities based on a likelihood that the patient is physically available to take the medication, wherein the likelihood that the patient is physically available is based on the patient's physical ability to take the medication, wherein the likelihood that the patient's physical ability to take the medication is based on a physical restriction, wherein the physical restriction comprises a physical requirement to take the medication,
    generating a physical availability model based on the plurality of opportunities weighted based on the likelihood that the patient is physically available to take the medication, and
    combining the cognitive availability model and the physical availability model to generate the total availability model;
  determine a suggested arrangement for the patient to take the medication based on the total availability model, wherein the suggested arrangement comprises the opportunity with the highest likelihood that the patient is available to take the medication and will react to take the medication;
  generate an alert corresponding to the suggested arrangement for the patient to take the medication;
  provide the alert to a user device associated with the patient;
  receive a response from the user device, wherein the response indicates whether or not the patient will take the medication; and
  train the total availability model based on the response and the time the response was provided to the user device.

13. The computer implemented method of claim 1, wherein the likelihood that the patient is cognitively available is based on an expected duration of the activity.

14. The computer implemented method of claim 13, wherein the likelihood that the patient is cognitively available to take the medication is greater for activities that take less time and the likelihood that the patient is cognitively available to take the medication is lesser for activities that take more time.

15. The computer implemented method of claim 14, wherein the likelihood that the patient is cognitively available to take the medication is greater when the patient is engaged in viewing a weather application and the likelihood that the patient is cognitively available to take the medication is lesser when the patient is engaged in viewing a game application.

16. The computer program product of claim 7, wherein the likelihood that the patient is cognitively available to take the medication is based on an expected duration of the activity.

17. The computer program product of claim 16, wherein the likelihood that the patient is cognitively available to take the medication is greater for activities that take less time and the likelihood that the patient is cognitively available to take the medication is lesser for activities that take more time.

18. The computer program product of claim 17, wherein the likelihood that the patient is cognitively available to take the medication is greater when the patient is engaged in viewing a weather application and the likelihood that the patient is cognitively available to take the medication is lesser when the patient is engaged in viewing a game application.

* * * * *